United States Patent [19]

Fossli et al.

[11] Patent Number: 4,956,344
[45] Date of Patent: Sep. 11, 1990

[54] METHOD FOR TREATMENT OF LESIONS IN THE LARGE INTESTINAL EPITHELIUM WITH A TRIPEPTIDE

[75] Inventors: Tellef Fossli, Nissedal; Karl L. Reichelt; Øyvind Skraastad, both of Oslo; Paul D. Edminson, Rykkinn, all of Norway

[73] Assignee: Hafslund Nycomed A/S, Oslo, Norway

[21] Appl. No.: 304,904

[22] Filed: Feb. 1, 1989

Related U.S. Application Data

[63] Continuation of Ser. No. 098,059, Sep. 17, 1987, abandoned.

[51] Int. Cl.$^5$ .............................................. A61K 37/02
[52] U.S. Cl. ......................................... 514/18; 514/2; 514/12; 530/331
[58] Field of Search ................... 530/331, 828; 514/18, 514/908, 21, 2

[56] References Cited

U.S. PATENT DOCUMENTS 4,260,601 4/1981 Reichelt et al. ...................... 530/331

FOREIGN PATENT DOCUMENTS 2075516 11/1981 United Kingdom ................ 530/331

OTHER PUBLICATIONS

Skraastad et al., Carcinogenesis, vol. 10, No. 1, pp. 79-82 (1982).
Levine et al., Proceedings of AALR, vol. 27, (1986), p. 211.
May et al., American Physiological Society, 241, pp. 520-529 (1981).
Sassier et al., Cell Tissue Kinet., vol. 13, pp. 251-261, (1980).
Sassier et al. Cell Tissue Kinet., vol. 11, pp. 641-650, (1978).
Tufton, Cell Tissue Kinet., vol. 6, pp. 211-216, (1973).
Brugal et al., Cell Tissue Kinet., vol 8, pp. 171-187, (1975).
Kanagalingan et al., Chalones, Houck (ed) Amsterdam, Oxford, N.Y., North-Holland and Am. Elsevier, pp. 459-482 (1976).

Primary Examiner—Lester L. Lee
Assistant Examiner—T. Weissendorf
Attorney, Agent, or Firm—Wenderoth, Lind & Ponack

[57] ABSTRACT

A method for the treatment of hyperproliferative benign or malignant lesions in the large intestinal epithelium is provided.

The method comprises administering the tripeptide L-pyroglutamyl-L-histidyl-glycine of the formula:

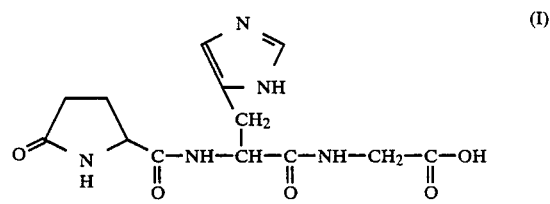

in which the pyroglutamyl and histidyl moieties are of the L-configuration.

1 Claim, No Drawings

METHOD FOR TREATMENT OF LESIONS IN THE LARGE INTESTINAL EPITHELIUM WITH A TRIPEPTIDE

This is a continuation of now abandoned application Ser. No. 098,059, filed Sept. 17, 1987.

BACKGROUND AND PRIOR ART

The present invention relates to a new medical use of a tripeptide and a composition containing said tripeptide.

The tripeptide is L-pyroglutamyl-L-histidyl-glycine of the formula

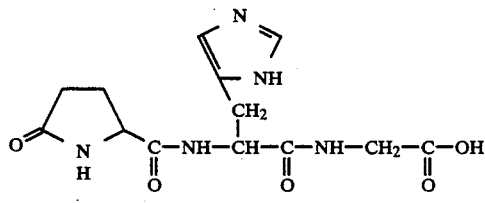

in which the pyroglutamyl and histidyl moieties are of the L-configuration.

This tripeptide is disclosed in U.S. Pat. No. 4,260,601, and it is stated therein that it has "interesting anorexigenic properties". In the patent it is stated that it is of potential interest for use against obesity caused by overeating. However, this patent has not yet been utilized commercially.

BRIEF SUMMARY OF THE INVENTION

The basis for the present invention is recent findings which have not previously been reported and which must be considered entirely unexpected and surprising in view of the prior art.

Thus, it has now been found that the tripeptide inhibits the normal cell proliferation and hyperproliferation (excessive and uncontrolled cell growth) causing benign and malignant lesions in the large intestinal epithelium, and it may therefore be useful for the treatment of certain diseases or lesions such as cancer.

DETAILED DESCRIPTION

Under physiological conditions epithelial cell loss from the luminal surface of the colon is balanced by cell replication in the lower part of the crypts. The pattern of cell proliferation in the large intestinal epithelium has been extensively studied in normal steady state cell renewal as well as after experimentally induced perturbations. In spite of this, the major factors that regulate normal cell renewal have remained largely unknown.

Partially purified inhibitors in tissue extracts made from the intestine or isolated intestinal epithelial cells have been shown to reduce the cell proliferation in the epithelia of the small and large intestine in vivo. [Brugal and Pelmont, (1975), Cell Tiss. Kinet. 8; Sassier and Bergeron, ibid 11: 641-650 (1978), and 13:251-261 (1980); Tutton, ibid 6:211-216 (1973)]. Also, in vitro experiments using a rat small intestinal epithelial cell line (May et al., 1981, Am. J. Physiol. 241:520-527) and colon carcinoma cell lines (Kanagalingam and Houck, 1976 In:Chalones, Houck, J. C. (ed) Amsterdam, Oxford, New York: North-Holland and American Elsevier 1976, pp 459-482; Levine et al., 1986, Proc. Annu. Meet. Am. Assos. Cancer Res. 27:211) indicate that both normal and malignant cells are susceptible to such endogenous inhibitors. However, the difficulties in purification and characterization of the inhibitors have been an obstacle to further examination of their biological properties and their importance as growth regulators. In order to obtain further evidence for the possible existence of endogenous inhibitors of cell proliferation in the large intestinal epithelium, we prepared aqueous extracts of mouse intestine. On finding a reversible inhibitory effect on intestinal cell proliferation of the crude extract, we proceeded with purification procedures until we were able to identify a tripeptide that acted in the same way as the crude extract. Further, we have dicovered that this tripeptide has the structure pGlu-His-Gly(OH) (see formula above), and that synthetic samples of this tripeptide show the same dose optimal for inhibitory effects on the large intestinal epithelium as does the purified biological extract.

EXPERIMENTAL PROCEDURES

All in vivo experiments were performed with hairless mice at 0800-0900 AM. The fractions were suspended in distilled water, slightly acidified (pH=6) and injected i.p. at different doses dependent on the purity of the fraction. The controls received solvent only. The pattern of cell proliferation after injecting the peptide was examined by varying the time between treatment and sacrifice.

To test for possible tissue specificity of the tripeptide the back skin and a defined part of ileum of eight animals were fixed immediately after killing. The mitotic rate (see below) in sections from these tissues was compared with the corresponding values in solvent-treated animals. Unilateral nephrectomy (uNX) was performed in four animals, and the animals were treated with the tripeptide at 18h after surgery. Controls underwent uNX and received solvent only. These animals received Colcemid 3h before sacrifice at 42h. The mitotic rate (number of accumulated metaphases per 1000 cells per 3h) was registered in the outer part of the kidney cortex.

Two hours before sacrifice (except for the experiments testing tissue specificity in the kidney) all animals received Colcemid 0.15 mg per animal i.p. $^3$HTdR (tritiated thymidine) was injected 30 minutes before sacrifice (30 $\mu$Ci per animal i.p.).

The effects of a hemoregulatory pentapeptide (U.S. Pat. No. 4,499,081) and of a mitosis-inhibiting pentapeptide isolated from mouse epidermis (WO 87/00180) were tested by examining the mitotic rates in the small and large intestine at a dose of $10^{-12}$ mole per animal in an identical experimental setting as described for the tripeptide.

CELL KINETIC MEASUREMENTS

Mitotic rate: After routine dehydration and paraffin embedding, sections were cut at 5 $\mu$m and stained with haematoxylin. Colcemid-arrested mitoses per 500 crypt cells were determined in ten longitudinally cut crypts in ileum and colon. Only crypts that were cut strictly longitudinally were accepted, viz., only those where the lumen of the crypt could be followed from the bottom of the gland to the lumen of the gut. No telophases were seen. The number of accumulated metaphases in epidermis Was determined by counting 25 vision fields of interfollicular epidermis (eyepiece 12.5, objective 40) and expressed as mitoses per vision field per 2h.

Labelling index: Paraffin sections, cut at 5 $\mu$m, were dipped in Kodak-NTB emulsion and exposed for 3 weeks at 0°-4° C., developed, and stained with haematoxylin The number of labelled cells were counted per 500 crypt cells in longitudinally cut crypts as described above. Similarly, the number of labelled cells in 40 vision fields of interfollicular epidermis (eyepiece 12.5, objective 40) was determined. A cell was considered labelled when the number of grains was five or more.

STATISTICS

All results were evaluated by the Wilcoxon rank sum test, and differences with a $p<0.05$ were considered significant.

The effect of the tripeptide on the mitotic rate in the large intestinal epithelium at different doses is shown in Table 1. At a dose of $10^{-12}$ mole per animal the number of accumulated metaphases was reduced by more than 50 %. A smaller, but significant inhibition was observed even at a dose of $10^{-11}$ mole per animal. Higher or lower doses gave no significant decrease in cell proliferation.

TABLE 1

The effect of various doses of the synthetic tripeptide PGlu-His-Gly(OH) on the cell proliferation in the large intestinal epithelium.

| | | Treated | SEM | Controls | SEM |
|---|---|---|---|---|---|
| $10^{-18}$ | mole per animal | 0.035 | 0.003 | 0.044 | 0.004 |
| $10^{-15}$ | mole per animal | 0.042 | 0.006 | 0.043 | 0.005 |
| $10^{-12}$ | mole per animal* | 0.018 | 0.001 | 0.042 | 0.003 |
| $10^{-11}$ | mole per animal* | 0.021 | 0.003 | 0.035 | 0.003 |
| $10^{-9}$ | mole per animal | 0.044 | 0.010 | 0.038 | 0.007 |
| $10^{-6}$ | mole per animal | 0.047 | 0.011 | 0.049 | 0.007 |

*p <0.05

Table 2 shows the time course of the mitotic rate in the large intestinal epithelium at 24h after a single i.p. injection of the peptide at a dose of $10^{-12}$ mole per animal. The number of accumulated metaphases was significantly reduced at 2-4h after injection. Thereafter, the mitotic count in the treated group exceeded the control level for a period of 6-8h (not formally significant). Subsequently, a new Wave of inhibition was observed approximately 15h after injection. This effect was less pronounced than the first.

Table 3 demonstrates the effect of the tripeptide on the labelling indices in the large intestinal epithelium. A pronounced reduction of the labelling index (LI) was seen at 4h after injection of the peptide. Here too, two periods of inhibitions were observed. Approximately 8h after the first decrease in the number of labelled cells a second inhibition of the same degree was observed. The reduced LI seen at 15 and 18th after treatment with the peptide is not statistically significant.

The pattern of cell proliferation after a single injection of synthetic tripeptide pGlu-His-Gly (OH) at a dose of $10^{-12}$ mole per animal (Time interval indicated)

TABLE 2

| Mitotic rate: | Treated | | Controls | |
|---|---|---|---|---|
| 2 h | 0.021* | 0.003 | 0.048 | 0.012 |
| 4 h | 0.018* | 0.001 | 0.042 | 0.004 |
| 6 h | 0.027 | 0.003 | 0.031 | 0.001 |
| 8 h | 0.031 | 0.010 | 0.025 | 0.004 |
| 12 h | 0.019 | 0.001 | 0.015 | 0.002 |
| 15 h | 0.010* | 0.002 | 0.022 | 0.004 |
| 18 h | 0.027 | 0.002 | 0.034 | 0.006 |
| 24 h | 0.057 | 0.010 | 0.061 | 0.009 |

TABLE 3

| Labelling index: | Treated | | Controls | |
|---|---|---|---|---|
| 2 h | 0.086 | 0.006 | 0.092 | 0.016 |
| 4 h | 0.067* | 0.009 | 0.11 | 0.003 |
| 6 h | 0.067 | 0.005 | 0.075 | 0.003 |
| 8 h | 0.058 | 0.013 | 0.054 | 0.008 |
| 12 h | 0.048* | 0.004 | 0.071 | 0.007 |
| 15 h | 0.068 | 0.008 | 0.084 | 0.010 |
| 18 h | 0.11 | 0.01 | 0.13 | 0.012 |
| 24 h | 0.098 | 0.013 | 0.086 | 0.005 |

The tests of tissue specifically were performed by examining the effect of the tripeptide on continuously proliferating epithelia (epidermis and the small intestine) and a stable cell population (kidney tubular epithelium), in which the cell proliferation was induced by contralateral nephrectomy. No inhibitory effect was observed in any of these tissues at the time and does levels tested.

The cell proliferation in the large intestinal epithelium was unchanged after the treatment with the epidermal pentapeptide pGlu-Glu-Asp-Ser-Gly (OH) (WO/87/00180), as with the hemoregulatory pentapeptide pglu-glu-Asp-Cys-Lys (U.S. Pat No. 4,499,081) at the doses and times tested. The inhibitory effect of the synthetic tripeptide on the mitotic rate in the large intestinal epithelium is shown in Table 4.

TABLE 4

Inhibitory effect of pGlu-His-Gly(OH) on the mitotic rate in the large intestinal epithelium (Result of seven identical experiments in mice).

Injection of pGlu-His-Gly(OH) at a dose of $10^{-12}$ mole per animal (synthetic peptide)

| Treated group* | | Controls | |
|---|---|---|---|
| Mean | SEM | Mean | SEM |
| 0.018 | 0.005 | 0.042 | 0.003 |
| 0.021 | 0.003 | 0.033 | 0.003 |
| 0.026 | 0.007 | 0.040 | 0.009 |
| 0.018 | 0.001 | 0.042 | 0.004 |
| 0.026 | 0.004 | 0.050 | 0.004 |
| 0.043 | 0.001 | 0.070 | 0.011 |
| 0.025 | 0.004 | 0.039 | 0.008 |

*p <0.05

In vitro studies on the effect of the tripeptide pGlu-His-GlYOH on the profileration of the colon carcinoma cell line HT 29.

Cell culture: HT 29 cells, 20000 cells per well in 96-well tissue culture clusters. Medium: RPMI 1640, 1 % fetal calf serum Concentration of the tripeptide $10^{-8}$M, lyophilized peptide dissolved in medium.

Assay for proliferation: Incorporation of tritiated thymidine ($^3$HTdR) 6 hour-period, $^3$HTdR 1 uCi per well.

The tripeptide was added to the culture on the third day (exponential growth), and the incorporation of tritiated thymidine was measured for 6 hour-periods at 16h, 24h, and 40h after the peptide was added to the wells.

The results are given as Mean and SEM in treated and control groups (Controls received 50 µl medium only)

| Time interval after addition of peptide | Controls | SEM | Treated | SEM |
|---|---|---|---|---|
| 16 h | 14295 | 1658 | 12177 | 499 |
| 24 h | 16430 | 1659 | 9080* | 1196 |

| Time interval after addition of peptide | Controls | SEM | Treated | SEM |
|---|---|---|---|---|
| 40 h | 11853 | 581 | 12485 | 1285 |

By using the peptide in $10^{-8}$M concentration, a significant reduction of the incorporation of $^3$HTdR was obtained 24–30h after the treatment. By increasing the serum addition to 10 & the results varied between significant inhibition of growth and no effect. (Possibly because of a stronger growth stimulus obtained by 10 % serum). The tripeptide at a concentration of $10^{-10}$M gave less, but still significant inhibition in the same assay.

The tripeptide used according to the present invention may be prepared in any convenient manner, for instance as described in U.S. Pat. No. 4,260,601, which is incorporated herein by reference.

The compositions according to the invention may have any of the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof Dosage units containing the compounds of this invention preferably contain 1–100 μg, for example 50 μg of the peptide of formula (I).

A further feature of the present invention is that a method is provided for inhibiting hyperproliferative benign or malignant lesions in the large intestinal epithelium which comprises the administration of an effective amount of a pharmaceutical composition as hereinabove defined to a subject

We claim:

1. A method for treatment of hyperproliferative benign or malignant lesions in the large intestinal epithelium which comprises administering to a subject having such lesions an effective amount to treat such lesions of the tripeptide L-pyroglutamyl-L-histidylglycine of the formula:

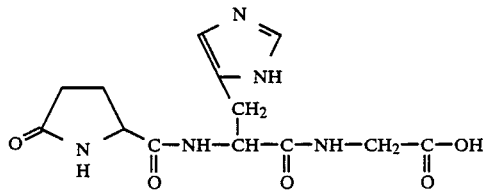

wherein the pyroglutamyl and histidyl moieties are of the L-configuration.

* * * * *